United States Patent [19]

Homan

[11] 3,935,310
[45] Jan. 27, 1976

[54] REMEDY FOR TREATMENT OF HEMORRHOIDS

[76] Inventor: John D. Homan, 115 Gilbert Ave., Ada, Ohio 45810

[22] Filed: Mar. 24, 1975

[21] Appl. No.: 561,632

Related U.S. Application Data

[63] Continuation-in-part of Ser. No. 448,820, March 7, 1974, abandoned.

[52] U.S. Cl. .............................................. 424/195
[51] Int. Cl.² ............................................ A61K 35/78
[58] Field of Search .................................... 424/195

[56] References Cited
UNITED STATES PATENTS

| | | | |
|---|---|---|---|
| 43,341 | 6/1864 | Roney et al. | 424/195 |
| 74,151 | 2/1868 | Sanderson | 424/195 |
| 79,411 | 6/1868 | Swarthout | 424/195 |
| 89,562 | 5/1869 | Curl et al. | 424/195 |

OTHER PUBLICATIONS

The Dispensatory of the U.S.A., The 24th Ed. by Osol et al., published by J. B. Lippincott Co. (1947), pp. 145–148, 620 and 1390.

*Primary Examiner*—Donald B. Moyer
*Attorney, Agent, or Firm*—Francis M. Crawford

[57] ABSTRACT

The present invention relates to a process for the treatment of hemorrhoids and to a composition therefor which comprises the product resulting from heating to a temperature of the order of 100° – 240°F, for a period of time of the order of 2 – 15 minutes, a mixture of the powdered or chipped limbs or roots of the shrub *Celastrus scandens*, commonly known as bittersweet, and an animal or vegetable fat. The preferred form of the composition is then strained to remove solid particles and mixed with a topical anesthetic, such as celery seed extract, and benzoin to retard the rancidity of the fat.

6 Claims, No Drawings

REMEDY FOR TREATMENT OF HEMORRHOIDS

This application is a continuation-in-part of my U.S. Ser. No. 448,820 filed Mar. 7, 1974 now abandoned.

The present application relates to the treatment of hemorrhoids and to a composition suitable therefor. More particularly, it relates to a composition suitable for the treatment of hemorrhoids and for the reduction and elimination of anoral inflammation caused thereby and comprising the product resulting from heating to a temperature of the order of 100°–240°F, for a period of time of the order of 2–15 minutes, a mixture of the powdered or chipped limbs or roots of the shrub *Celastrus scandens*.

Hemorrhoids is a rather common ailment of the anorectal area and may be either or both internal and external, causing in particular inflammation of the veins of the anorectal area and frequesntly accompanied by itching of varying degrees of intensity. Many remedies have been suggestied and tried for the alleviation of these ailments with varying degrees of success. Some have been partially effective in either reducing the inflammation or itching but few have been successful in reducing or completely eliminating both. Frequently, undesirable side-effects have resulted from such treatments and which have appreciably increased the difficulties in obtaining satisfactory relief.

In accordance with the present invention, the drawbacks and disadvantages of previous methods of treating hemorrhoids have been effectively overcome to a very large degree, both the inflammation and itching normally present in such disorders being effectively overcome after only a relatively short period of treatment, and without any unfavorable side-effects of the type experienced with previously used remedies and treatments.

The treatment of the present invention comprises essentially the application to the infected areas of an ointment containing certain unknown ingredients of the shrub *Celastrus scandens*. If desired the composition can be employed in suppository form. In either form, the composition preferably contains, in addition to the active ingredient, a conventional topical anesthetic such as, for example, celery seed extract, or other well-known topical anesthetics such as benzocaine, procaine base, or other equivalent material known to be effective as an anesthesia in the anorectal area.

The prior art has suggested the therapeutic utility of certain unknown compounds derived from *Celastrus scandens* by reaction with other materials but not of the derivatives per se of said *Celastrus scandens*. Roney et al (U.S. Pat. No. 43,341) boiled and reboiled a mixture of green beech bark, elder bark and leaves, bittersweet root and stalk, thornapple stalk and leaves, poke root, bean leaves and stalk, live-for-ever, rosin and lark. Swarthout (U.S. Pat. No. 79,411) melted over a slow fire a mixture of extract of bittersweet, turpentine, salt butter, beeswax and balsam of fir. Curl et al (U.S. Pat. No. 89,562) "stewed down" for a period of 30 minutes a mixture of lard, balm of Gilead buds and bark of bittersweet roots and then added quicksilver dissolved in nitric acid, spirits of turpentine and balsam of fir. Sanderson (U.S. Pat. No. 74,151) steeped in spirits a mixture of bittersweet root, stramonium leaves, cicuta leaves and the root of the deadly nightshade, then added lard and heated to evaporate to an ointment and finally added extract of hyoscyamus, extract of taraxacum, gum of opium, the resulting product to be used in combination with other medecines. It will be quite obvious that none of these involved the use of the product being claimed by applicant.

The new composition of the present invention is preferably used in ointment or suppository form, applied morning and night after defecation. Soon after application of the composition the pain and itching are alleviated and the bittersweet reduces congestion and inflammation and accelerates the normal healing process and assists in making bowel evacuation more comfortable.

A preferred method of preparing the new composition of the present invention comprises heating powdered or chipped bittersweet limbs, or preferably roots, with an animal fat or a vegetable oil, such as cottonseed or soya bean oil and removing the resulting solid material by screening, filtration or other suitable means after cooling to approximately 60°F. Optionally, but preferably, benzoin is then incorporated into the screened or filtered material for the purpose of retarding decomposition of the fat. This, however, is not an essential ingredient of the composition since the latter can be effectively used without such addition, the addition of the benzoin being desirable only when extended shelf life of the product is desired. When pain and itching are present, the above composition, with or without added benzoin, is then further cooled and mixed with a conventional anesthetic, such as, for example, celery seed extract or other suitable anesthetic. With or without the addition of the benzoin or topical anesthetic, the composition is ready for use in treating hemorrhoids.

In preparing the above new composition various types of animal fats and vegetable oils may be satisfactorily used. Suitable such materials include beef tallow, mutton tallow, pork lard, all types of vegetable shortenings, cottonseed oil, soya bean oil, and the like. Satisfactory compositions are obtained by heating 16–80 oz. of powdered or chipped *Celastrus scandens* limbs or roots per 100 pounds of animal fat or vegetable oil, the heating being effected at temperatures ranging from 100° to 240°F, for periods of time ranging from approximately 2 to 15 minutes. When heated to temperatures of 260°F, or for longer periods of time at elevated temperatures, the fat or oil is usually "burned", thus making the resulting composition less desirable for use. When benzoin is incorporated into the composition amounts of the oorder of 100–200 grams per 100 pounds of fat or oil, depending in general upon the atmospheric temperature, will satisfactorily retard the rancidity of the fat or oil.

When a topical anesthetic is incorporated into the composition it is generally used in amounts of the order of 25–200 grams per 100 pounds of fat or oil. Such amounts of celery seed extract have been found to give particularly effective results.

The following specific examples are given to illustrate specific compositions of the type described above which have been found to give particularly desirable results in the treatment of hemorrhoids. Excellent results were obtained with all of these compositions when applied as above described over periods of time ranging from 5 to 30 days, depending upon the particular individual and the severity of the ailment.

EXAMPLE I

A mixture of 16 oz. of chipped *Celastrus scandens* roots 100 lbs of beef tallow was heated for 15 minutes to a temperature of 230°F, cooled to 60°F, strained to remove solid particles and ⅛ oz of celery seed extract incorporated as above described.

EXAMPLE II

In this experiment the following ingredients were used and the composition was prepared as described in Example I.

80 oz powdered *Celastrus scandens* roots and limbs
100 lbs of mutton tallow
⅛ oz celery seed extract
100 grams of Benzoin.

EXAMPLE III

In this experiment, the operation was carried out as above described using the following materials:

16 oz powdered *Celastrus scandens* root
25 lbs of vegetable shortening
⅛ oz celery seed extract
25 grams Benzoin.

The mixture of *Celastrus scandens* root powder and vegetable shortening was heated in a pressure cooker for a period of 5 minutes at a temperature of 150°F, and then cooled to a temperature of approximately 60°F, the benzoin then added with good stirring. The resulting mixture was then allowed to stand for ½–2 hours and then strained to remove solid particles. The resulting product was then permitted to cool until the mass congealed, celery seed extract then added and the resulting mixture homogenized to obtain thorough mixture.

EXAMPLE IV

In this experiment the following ingredients were used:

12 grams of powdered *Celastrus scandens* root
225 grams of corn oil

After heating the resulting composition and filtering the product was a liquid difficult to apply. It could, however, be whipped into a gel with a starch base giving a product which could be effectively used in ointment form.

EXAMPLE V

The composition prepared as above described using the following ingredients gave a composition having excellent curative properties:

24 grams of powdered *Celastrus scandens* root
225 grams of corn oil

Effective curative results were obtained in general with *Celastrus scandens* in powdered or chipped form treated as above described, although in some instances the physical form of the compositions made the latter difficult to use, the more desirable compositions being of a physical form which could be applied in ointment form. This, however, was largely a matter of convenience. The preferred form of product contained a topical anesthetic, preferably celery seed extract. Where the fat or oil used in making the composition was subject to becoming rancid upon standing, the final product desirably contained a rancidity inhibitor, such as benzoin.

What is claimed is:

1. Composition for the treatment of hemorrhoids consisting essentially in the product resulting from heating powdered or chipped limbs or roots of *Celastrus scandens* to a temperature not substantially exceeding 240°F, for a period of 2–15 minutes, in a medium selected from the group consisting of animal fats and vegetable oils.

2. Composition according to claim 1, wherein said composition results from the heating of 16–80 ounces of powdered or chipped limbs of roots of *Celastrus scandens* for 2–15 minutes, at a temperature of 100–240°F in 100 pounds of a medium selected from the group consisting of animal fats and vegetable oils.

3. Composition according to claim 1, wherein the solid products in said heated composition have been removed by straining prior to use.

4. Composition according to claim 1, wherein said composition additionally contains 25–200 grams of a topical anesthetic per 100 pounds of said animal fat or vegetable oil.

5. Composition according to claim 1, wherein said composition additionally contains 25–200 grams of celery seed extract, per 100 pounds of said animal fat or vegetable oil.

6. Composition according to claim 1, wherein said composition additionally contains 25–200 grams of celery seed extract and 100–200 grams of benzoin per 100 pounds of animal fat or vegetable oil.

* * * * *